United States Patent
Siskin et al.

(10) Patent No.: US 7,524,990 B2
(45) Date of Patent: Apr. 28, 2009

(54) SYNTHESIS OF STERICALLY HINDERED SECONDARY AMINOETHER ALCOHOLS

(75) Inventors: Michael Siskin, Randolphr, NJ (US); Alan Roy Katritzky, Gainesville, FL (US); Kostyantyn Mykolayevich Kirichenko, Gainesville, FL (US); Adeana Richelle Bishop, Baton Rouge, LA (US); Christine Nicole Elia, Bridgewater, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 189 days.

(21) Appl. No.: 10/587,207

(22) PCT Filed: Feb. 1, 2005

(86) PCT No.: PCT/US2005/003053

§ 371 (c)(1),
(2), (4) Date: May 24, 2007

(87) PCT Pub. No.: WO2005/082835

PCT Pub. Date: Sep. 9, 2005

(65) Prior Publication Data

US 2007/0293705 A1    Dec. 20, 2007

Related U.S. Application Data

(60) Provisional application No. 60/545,117, filed on Feb. 17, 2004.

(51) Int. Cl.
    C07C 209/22    (2006.01)
(52) U.S. Cl. .................. 564/393; 564/395; 564/396; 564/468; 564/469; 564/474
(58) Field of Classification Search .................. None
    See application file for complete search history.

(56) References Cited

U.S. PATENT DOCUMENTS

| | | | |
|---|---|---|---|
| 4,112,051 A | 9/1978 | Sartori et al. | |
| 4,112,052 A | 9/1978 | Sartori et al. | |
| 4,405,585 A | 9/1983 | Sartori et al. | |
| 4,417,075 A | 11/1983 | Stogryn | |
| 4,471,138 A | 9/1984 | Stogryn | |
| 4,487,967 A | 12/1984 | Stogryn et al. | |
| 4,508,692 A | 4/1985 | Savage et al. | |
| 4,618,481 A | 10/1986 | Heinzelmann et al. | |
| 4,892,674 A | 1/1990 | Ho et al. | |
| 4,894,178 A | 1/1990 | Ho et al. | |
| 4,961,873 A | 10/1990 | Ho et al. | |
| 5,098,604 A | 3/1992 | Brouard et al. | |
| 5,874,623 A | 2/1999 | Adkins et al. | |
| 7,351,865 B2 * | 4/2008 | Siskin et al. | 564/468 |
| 7,429,680 B2 * | 9/2008 | Siskin et al. | 564/468 |
| 2007/0287866 A1 * | 12/2007 | Siskin et al. | 564/468 |

FOREIGN PATENT DOCUMENTS

| | | |
|---|---|---|
| GB | 2 017 524 | 10/1979 |
| WO | WO 2005/081777 | 9/2005 |
| WO | WO 2005/082836 | 9/2005 |
| WO | WO 2005/082837 | 9/2005 |

OTHER PUBLICATIONS

Frazier and Kohl, "Selective Absorption of Hydrogen Sulfide from Gas Streams", Industrial and Engineering Chemistry, Nov. 1950, pp. 2288-2292, vol. 42, No. 11, The Fluor Corporation Ltd., Los Angeles, California.

Overberger and Sarlo, "Mixed Sulfonic-Carboxylic Anhydrides", J. Am. Chem. Soc., Mar. 4, 1963, pp. 2446-2448, vol. 85.

Karger and Mazur, "Cleavage of Ethers by Mixed Sulfonic-Carboxylic Anhydrides", J. Am. Chem. Soc., Jul. 3, 1968, pp. 3878-3879, 90:14.

* cited by examiner

Primary Examiner—Brian J Davis

(57) ABSTRACT

Severely sterically hindered secondary aminoether alcohols are prepared by reacting organic carboxylic, organic carboxylic acid halides, acid anhydrides or a ketene with an alkyl, alkaryl or alkylhalo sulfonate to yield a sulfonic-carboxylic anhydride compound which is then reacted with a dioxane to cleave the ring of the dioxane, yielding a cleavage product which cleavage product is then aminated with an alkylamine and hydrolyzed with base to yield the severely sterically hindered secondary aminoether alcohol.

12 Claims, No Drawings

SYNTHESIS OF STERICALLY HINDERED SECONDARY AMINOETHER ALCOHOLS

This application is the U.S. National Phase filing of PCT Application No. PCT/US2005/003053 filed Feb. 1, 2005, which claims priority to U.S. Provisional Patent Application No. 60/545,117 filed Feb. 17, 2004.

FIELD OF THE INVENTION

The present invention relates to a method for the preparation of severely sterically hindered secondary aminoether alcohols which are useful in the removal of hydrogen sulfide from gaseous streams containing hydrogen sulfide and which may also contain carbon dioxide.

DESCRIPTION OF RELATED ART

It is well-known in the art to treat gases and liquids, such as mixtures containing acidic gases including $CO_2$, $H_2S$, $CS_2$, HCN, COS and oxygen and sulfur derivatives of $C_1$ to $C_4$ hydrocarbons with amine solutions to remove these acidic gases. The amine usually contacts the acidic gases and the liquids as an aqueous solution containing the amine in an absorber tower with the aqueous amine solution contacting the acidic fluid countercurrently. Usually this contacting results in the simultaneous removal of substantial amounts of both the $CO_2$ and $H_2S$. U.S. Pat. No. 4,112,052, for example, utilizes a sterically hindered amine to obtain nearly complete removal of $CO_2$ and $H_2S$ acid gases. This process is particularly suitable for systems in which the partial pressures of the $CO_2$ and related gases are low. For systems where the partial pressure of $CO_2$ is high or where there are many acid gases present, e.g., $H_2S$, COS, $CH_3SH$, $CS_2$, etc., a process utilizing an amine in combination with a physical absorbent, referred to as a "non-aqueous solvent process" is practiced. Such a system is described in U.S. Pat. No. 4,112,051.

Selective removal of $H_2S$ from acid gas systems containing both $H_2S$ and $CO_2$, however, is very desirable. Such selective removal results in a relatively high $H_2S/CO_2$ ratio in the separated acid gas which facilitates the subsequent conversion of the $H_2S$ to elemental sulfur in the Claus process.

The typical reactions of aqueous secondary and tertiary amines with $CO_2$ and $H_2S$ can be represented as follows:

$$H_2S + R_3N \rightleftharpoons R_3NH^+ + HS^-$$
$$H_2S + R_2NH \rightleftharpoons R_2NH_2^+ + HS^-$$
$$CO_2 + R_3N + H_2O \rightleftharpoons R_3NH^+ + HCO_3^-$$
$$CO_2 + 2R_2NH \rightleftharpoons R_2NH_2^+ + R_2NCO_2^-$$

where R is the same or different organic radical and may be substituted with a hydroxyl group. Because the reactions are reversible they are sensitive to the $CO_2$ and $H_2S$ partial pressures which is determinative of the degree to which the reactions occur.

Selective $H_2S$ removal is particularly desirable in systems having low $H_2S/CO_2$ ratios and relatively low $H_2S$ partial pressures as compared to that of the $CO_2$. The ability of amine to selectivity remove $H_2S$ in such systems is very low.

Solutions of primary and secondary amines such as monoethanol-amine (MEA), diethanolamine (DEA), diisopropanolamine (DPA), and hydroxyethoxyethylamine (DEA) absorb both $H_2S$ and $CO_2$, and thus have proven unsatisfactory for the selective removal of $H_2S$ to the exclusion of $CO_2$. The $CO_2$ forms carbamates with such amines relatively easily.

$H_2S$ has been selectively removed from gases containing $H_2S$ and $CO_2$ by use of diisopropanolamine (DIPA) either alone or mixed with a non-aqueous physical solvent such as sulfolane. Contact times, however, must be kept short to take advantage of the faster reaction of $H_2S$ with the amine as compared to the rate of $CO_2$ reaction with the amine.

Frazier and Kohl, Ind. and Eng. Chem., 42, 2288 (1950) showed that the tertiary amine methydiethanolamine (MDEA) is more selective toward $H_2S$ absorption as compared to $CO_2$. $CO_2$ reacts relatively slowly with tertiary amines as compared to the rapid reaction of the tertiary amine with $H_2S$. However, it has the disadvantage of having a relatively low $H_2S$ loading capacity and limited ability to reduce the $H_2S$ content to the desired level at low $H_2S$ pressures encountered in certain gases.

UK Patent Publication No. 2,017,524A discloses the use of aqueous solutions of dialkylmonoalkanolamines, e.g., diethylmonoethanol amine (DEAE), for the selective removal of $H_2S$, such material having higher selectivity and capacity for $H_2S$ removal at higher loading levels than MDEA. DEAE, however, has the disadvantage of a low boiling point of 161° C., making it relatively highly volatile resulting in large material loss.

U.S. Pat. No. 4,471,138 the entire teaching of which is incorporated herein by reference, teaches severely sterically hindered acyclic secondary aminoether alcohols having a high selectivity for $H_2S$ compared to $CO_2$. Selectivity is maintained at high $H_2S$ and $CO_2$ loadings.

The severely sterically hindered acyclic amine ether alcohols of U.S. Pat. No. 4,471,138 are represented by the general formula:

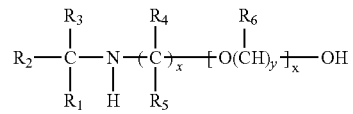

wherein $R_1$ and $R_2$ are each independently selected from the group consisting of alkyl and hydroxyalkyl radicals having 1-4 carbon atoms, $R_3$, $R_4$, $R_5$ and $R_6$ are each independently selected from the group consisting of hydrogen, alkyl, and hydroxyalkyl radicals having 1-4 carbon atoms, with the proviso that at least one of $R_4$ or $R_5$ bonded to the carbon atom which is directly bonded to the nitrogen atom is an alkyl or hydroxyalkyl radical when $R_3$ is hydrogen, x and y are each positive integers ranging from 2-4, and z is a positive integer ranging from 1-4. These materials are prepared by a high temperature reaction preferably in the presence of a solvent, of a secondary or tertiary alkyl primary amine with an ether alcohol containing a carbonyl functionality in the presence of a source of hydrogen or with a haloalkoxyalkanol. Preferably the composition is of the general formula:

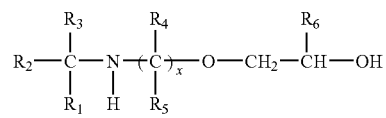

wherein:

$R_1 = R_2 = R_3 = CH_3$—; $R_4 = R_5 = R_6 = H$;

$R_1 = R_2 = R_3 = CH_3$—; $R_4 = H$ or $CH_3$; $R_5 = R_6 = H$;

$R_1=R_2=R_3=R_6=CH_3-$; $R_4=R_5=H$;

$R_1=R_2=R_3=CH_3CH_2-$; $R_4=R_5=R_6=H$; or $R_1 \ne R_2 \ne R_3 = H, CH_3-, CH_3CH_2-$; $R_4 \ne R_5 \ne R_6 = H, CH_3-$;

and where x=2 or 3.

U.S. Pat. No. 4,487,967 is directed to a process for preparing severely sterically hindered secondary aminoether alcohols by reacting a primary amino compound with a polyalkenyl ether glycol in the presence of a hydrogenation catalyst at elevated temperatures and pressures. The primary amino compounds employed have a general formula:

where $R^1$ is selected from the group consisting of secondary or tertiary alkyl radicals having 3 to 8 carbon atoms or cycloalkyl radicals having 3 to 8 carbon atoms. The polyalkenyl ether glycols employed have the general formula:

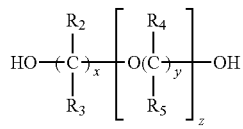

where $R_2$, $R_3$, $R_4$ and $R_5$ are each independently selected from the group consisting of hydrogen, $C_1$-$C_4$ alkyl radicals, and $C_3$-$C_8$ cycloalkyl radicals, with the proviso that if the carbon atom of $R_1$ directly attached to the nitrogen atom is secondary, at least one of $R_2$ and $R_3$ directly bonded to the carbon which is bonded to the hydroxyl group is as alkyl or cycloalkyl radical, x and y are each positive integers independently ranging from 2 to 4 and z is from 1 to 10, preferably 1 to 6, more preferably 1 to 4. The process is carried out in the presence of a catalytically effective amount of a supported Group VIII metal containing hydrogenation catalyst at elevated temperatures and pressure and the mole ratio of amino compound to polyalkenyl ether glycol is less than 2:1 when z is greater than 1.

SUMMARY OF THE INVENTION

A new process has been discovered for the production of severely sterically hindered secondary aminoether alcohols of the general formula 1:

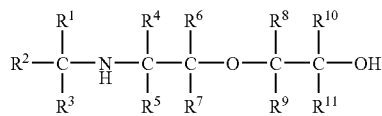

wherein $R^1$ and $R^2$ are each independently selected from the group consisting of alkyl and hydroxyalkyl radicals having 1 to 4 carbon atoms, preferably 1 to 2 carbon atoms, or $R^1$ and $R^2$ in combination with the carbon atom to which they are attached form a cycloalkyl group having 3 to 8 carbons; $R^3$ is selected from the group consisting of hydrogen, alkyl or hydroxyalkyl radicals having 1 to 4 carbon atoms, and mixtures thereof, preferably 1 to 2 carbon atoms, preferably alkyl or hydroxyalkyl radicals having 1 to 4 carbon atoms, more preferably 1 to 2 carbon atoms; $R^4$, $R^5$, $R^6$, $R^7$, $R^8$, $R^9$, $R^{10}$, and $R^{11}$ are the same or different and are selected from hydrogen, alkyl or hydroxyalkyl radicals having 1 to 4 carbon atoms, preferably 1 to 2 carbon atoms, or cycloalkyl radicals having 3 to 8 carbons; $R^4$, $R^5$, $R^6$, $R^7$, $R^8$, $R^9$, $R^{10}$, and $R^{11}$ are preferably hydrogen provided that when $R^3$ is hydrogen at least one of $R^4$ and $R^5$ directly bonded to the carbon which is bonded to the nitrogen atom is an alkyl or hydroxyalkyl radical. The process involves reacting an organic carboxylic acid halide, an organic carboxylic acid anhydride, a ketene or a mixture of any two or of all three thereof of the formula:

 (2a)

 (2b)

 (2c)

wherein $R^{12}$ and $R^{13}$ are the same or different and each is selected from the group consisting of alkyl radicals having 1 to 4 carbon atoms, preferably 1 to 2 carbon atoms, most preferably methyl, or aryl radicals, preferably phenyl substituted with hydrogen, one or more alkyl radicals having 1-10 carbon atoms, preferably 1-4 carbon atoms, most preferably methyl in the para position, and mixtures thereof, and X is a halogen selected from F, Cl, Br, I, and mixtures thereof, preferably Cl, and $R^x$ and $R^y$ are the same or different and are selected from the group consisting of hydrogen or alkyl radicals having 1 to 4 carbons, preferably 1 to 2 carbons, aryl radicals, preferably aryl radicals bearing substituents selected from the group consisting of hydrogen and one or more alkyl radicals having 1 to 10 carbons, preferably 1 to 4 carbons, and mixtures thereof, or $R^x$ and $R^y$ in combination with the carbon to which they are attached from a cycloalkyl radical having 3 to 8 carbons, preferably $R^x$ and $R^y$ are hydrogen or phenyl with an organic sulfonic acid of the formula:

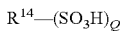

wherein Q is an integer selected from 1 to 4, preferably 1-3, more preferably 1-2, most preferably 1, $R^{14}$ is selected from the group consisting of alkyl radicals having 1 to 4 carbon atoms, preferably 1 to 2 carbon atoms, most preferably methyl, haloalkyl radicals of the formula $C_nH_{(2n+1)-z}X_z$ wherein n is 1 to 4 preferably 1 to 2, and most preferably 1; X is selected from the group consisting of F, Cl, Br, I, and mixtures thereof, preferably F and Cl, most preferably F; and z ranges from 1 to 5, preferably 1 to 3, most preferably 3, aryl radical 3

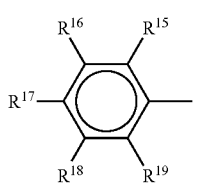

wherein $R^{15}$, $R^{16}$, $R^{17}$, $R^{18}$, and $R^{19}$ are the same or different and are selected from hydrogen and alkyl radicals having 1 to 20 carbon atoms, preferably $R^{15}$, $R^{16}$, $R^{18}$, and $R^{19}$ are hydrogen and $R^{17}$ is selected from hydrogen and alkyl radicals having 1-4 carbons, preferably 1 to 2 carbons, more preferably methyl, and mixtures thereof, to yield sulfonic-carboxylic anhydride compounds of the formula 4:

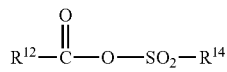
4a

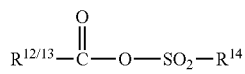
4b

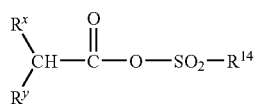
4c wherein $R^{12/13}$ means that in the product the R group can be $R^{12}$ or $R^{13}$ or a mixture thereof which is then reacted with a dioxane of the formula 5:

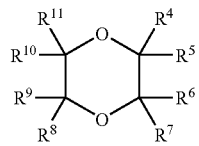
5 wherein $R^4$, $R^5$, $R^6$, $R^7$, $R^8$, $R^9$, $R^{10}$, and $R^{11}$ are the same or different and are selected from hydrogen, alkyl and hydroxyalkyl radicals having 1 to 4 carbons, preferably 1 to 2 carbons or cycloalkyl radicals having 3 to 8 carbons, more preferably $R^4$, $R^5$, $R^6$, $R^7$, $R^8$, $R^9$, $R^{10}$, and $R^{11}$ are hydrogen, to yield material of the general formula 6,

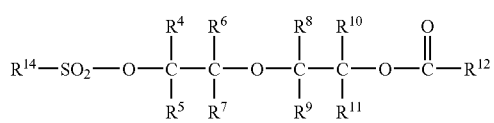
6a

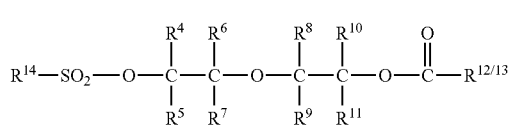
6b

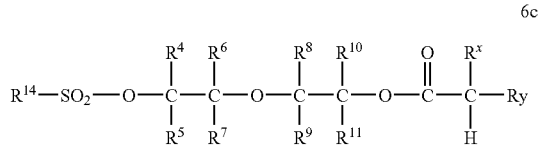
6c or mixtures thereof. It is not necessary that the product from each reaction step

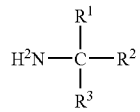
7 be isolated before being reacted with the reactant of a subsequent step up to this point. A cleavage product is still produced. The mixing of the organic carboxylic acid halide, organic carboxylic acid anhydride, ketene or mixture of any two or of all three thereof with the organic sulfonic acid and the dioxane can be in any order or sequence. Thus, the anhydride, acid halide, ketene or mixture of any two or all three can be mixed with the organic sulfonic acid and then mixed with the dioxane, or the dioxane can be first mixed with the organic sulfonic acid and then with the anhydride, acid halide, ketene or mixture of any two or all three thereof, or the anhydride, acid halide, ketene or mixture of any two or of all three thereof, can be mixed with the dioxane followed by the addition of the organic sulfonic acid. Thus the combination of the anhydride, acid halide, ketene or mixture of any two or of all three thereof with the dioxane and the organic sulfonic acid can be combined into a single reaction mixture and reacted as a mixture resulting in the one step production of the desired cleavage product. The cleavage product is then reacted with an alkylamine of the formula 7, wherein $R^1$, $R^2$ and $R^3$ are as previously defined to yield material of the general formula 8:

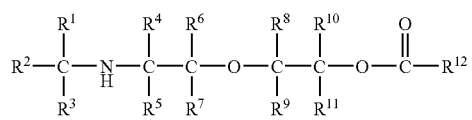
8a

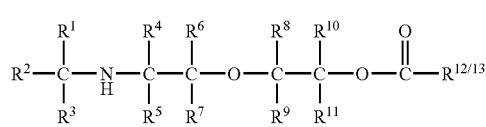
8b

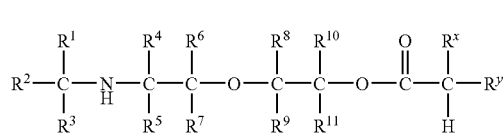
8c or mixtures thereof, which is subsequently hydrolyzed with a base to yield 1

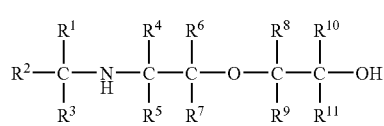
1

The preferred compounds defined by the general formula above include:

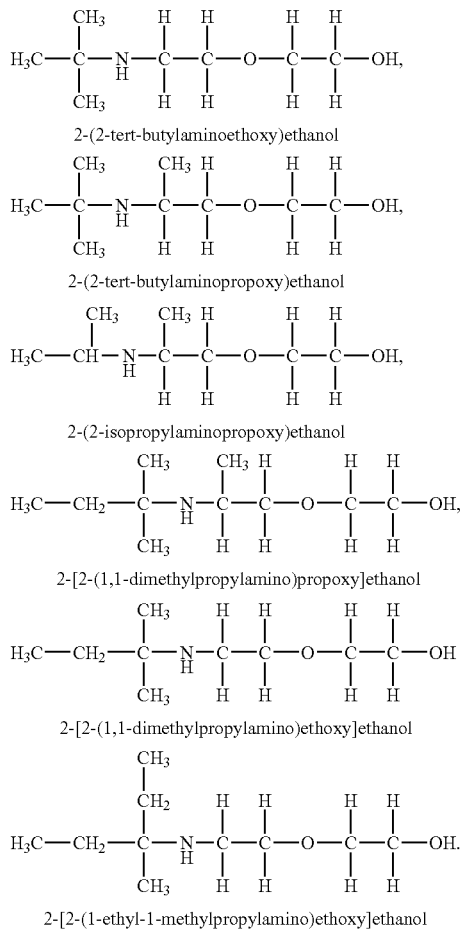

Typical starting materials to use as the first component are:

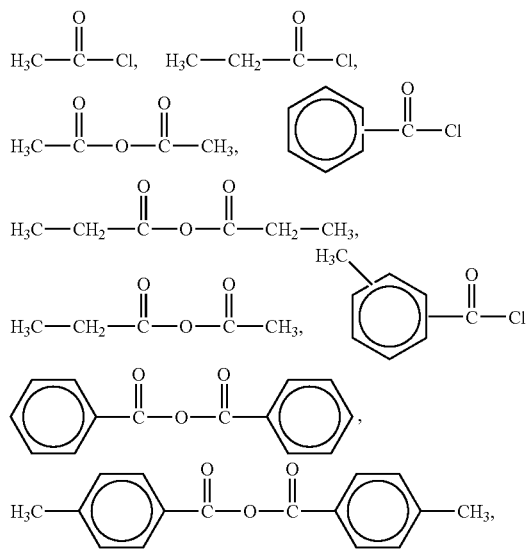

and ketenes which are typically

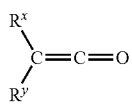

wherein $R^x$ and $R^y$ are the same or different and are hydrogen or alkyl radicals having from 1 to 4 carbons, preferably 1 to 2 carbons, most preferably hydrogen or aryl radicals, preferably aryl radicals substituted with hydrogen or one or more alkyl radicals having 1 to 10 carbons, preferably 1 to 4 carbons, or $R^x$ and $R^y$ in combination with the carbon to which they are attached from a cycloalkyl radical having 3 to 8 carbons, preferably $R^x$ and $R^y$ are hydrogen or phenyl the preferred ketenes being

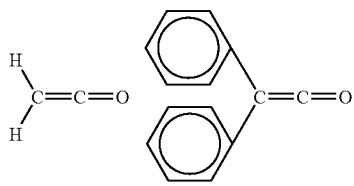

The ketenes useful in the present invention can be prepared employing any of the processes typical in the art. Thus, for example, acetic acid can be subjected to high temperature dehydration in the presence of $AlPO_4$, or acetone can be subjected to pyrolysis at from 500 to 750° C. to yield ketene and methane.

These materials are then reacted with a second component, typically

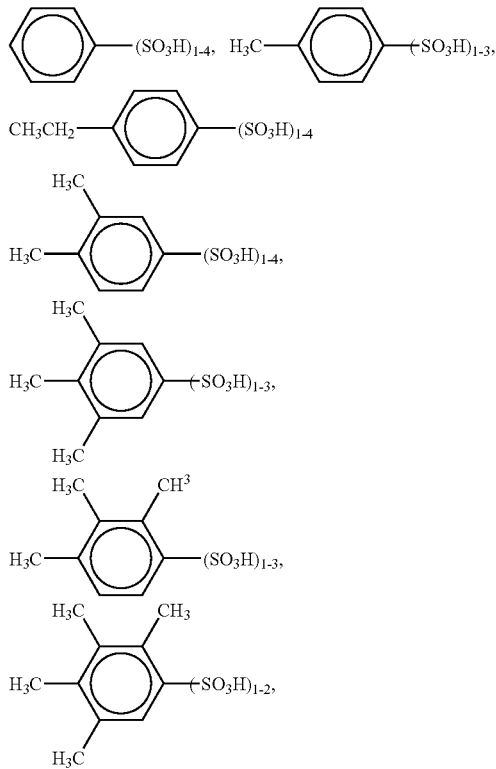

-continued

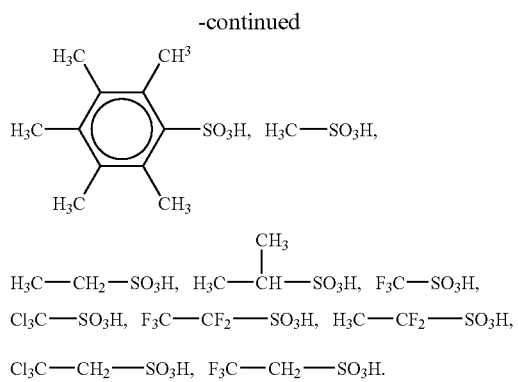

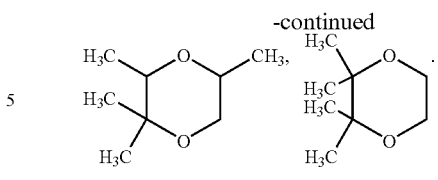

Other substituted isomers can be readily envisioned. Preferably, the 1,4-dioxane is

Other materials of the type described above can be readily envisioned.

The reaction of two such components yields acyl sulfonates 4a and/or 4b and/or 4c. The reaction can be carried out at a temperature in the range of about −20° C. to 150° C., preferably about 0° C. to 140° C., more preferably about 20° C. to 125° C. and at a pressure between about 1 bar to 100 bars, preferably about 1 bar to 50 bars, more preferably about 1 bar to 10 bars. The reaction can be carried out in the absence of any solvent or an inert solvent such as sulfolane, hexanes, acetonitrile can be used. Preferably, the dioxane for the subsequent cleavage reaction is used as the solvent resulting in a unified first step wherein the reaction mixture contains the acid anhydride, acid halide, ketene or mixture of any two or of all three thereof, the organic sulfonic acid and the dioxane. This reaction mixture is then reacted under the conditions subsequently described for the dioxane cleavage reaction.

The sulfonate 4 is reacted with a dioxane, which is typically of the formula:

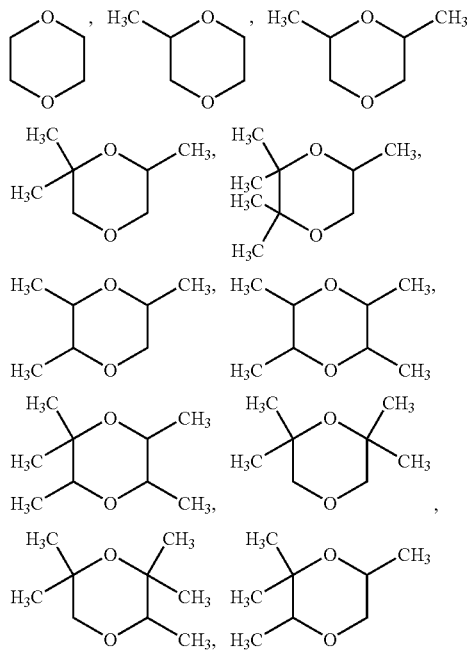

Reaction is for a time sufficient to cleave the dioxane ring and to achieve about 60-90% conversion to product. The dioxane also serves as the solvent for the reaction. The molar ratio of dioxane to sulfonate can range from about 1:1 to about 10:1, preferably about 1:1 to about 8:1, most preferably about 1:1 to about 5:1. The reaction can be carried out in the absence of any added solvent, e.g., the dioxane serving as the solvent, or an additional solvent such as acetonitrile or toluene can be used, the reaction being conducted at temperatures between about 50° C. to about 200° C., preferably about 70° C. to about 160° C., more preferably about 80° C. to about 140° C.

Preferably, the reaction is carried out in the absence of any added solvent at a temperature in the range of about 50° C. to about 160° C., preferably about 70° C. to about 160° C., more preferably about 80° C. to about 140° C.

The production of sulfonic-carboxylic anhydrides by the reaction of organic carboxylic acid halides or anhydrides with an organic sulfonic acid, and the cleaving of dioxone by such sulfonic-carboxylic anhydrides are described in greater detail by Karger and Mazur in "The Cleavage of Ethers by Mixed Sulfonic-Carboxylic Anhydrides", Journal of the American Chemical Society, 1968, 90, 3878-3879. See also "Mixed sulfonic-carboxylic anhydrides. I. Synthesis and thermal stability. New syntheses of sulfonic anhydrides" Journal of Organic Chemistry, 1971, 36, 528, and "Mixed sulfonic-carboxylic anhydrides. II. Reactions with aliphatic ethers and amines" Journal of Organic Chemistry, 1971, 36, 532.

The cleavage product 6 is then aminated with an amine 7 typically of the formula:

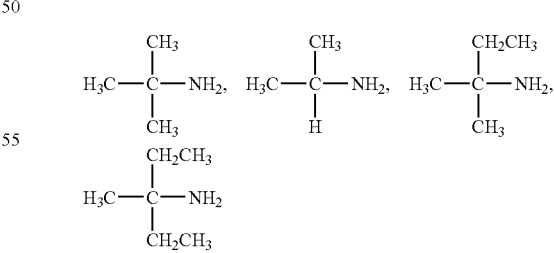

for a time sufficient to replace the —O—SO$_2$—R$^{14}$ group in cleavage product 6 by the amine 7. In general, the amine to cleavage product sulfonate group ratio is in the range of about stoichiometric to about 10:1, preferably about stoichiometric to about 8:1, more preferably about stoichiometric to about 4:1.

This amination step can be carried out under any conditions typical in the art. Amination can be conducted at atmospheric or at elevated pressure, elevated pressure being especially suitable when amination is performed using relatively low boiling amines such as t-butyl amine.

The amination can be conducted at pressures of from about atmospheric (1 bar) to about 100 bars, preferably about 1 to about 50 bars, and at temperatures of from about 40° C. to about 200° C., preferably about 40° C. to about 125° C. The amination can be performed using reflux, but this is not absolutely necessary. An inert solvent can be optionally used, such as benzene, toluene, diethyl ether, hexane, and the like.

Finally, the resultant of the amination step, product 8, is hydrolyzed using a base to yield the final desired product 1. Typical bases include an alkali metal hydroxide, an alkali metal carbonate, or an alkali metal alkoxide, such as sodium hydroxide, sodium carbonate, sodium methoxide, sodium tert-butoxide, etc. Reaction is preferably conducted at from about 20° C. to about 110° C., preferably about 20° C. to about 50° C. The process can be conducted under reflux.

Use of a solvent is optional for the hydrolysis reaction, one being used if the reactants are not already in the liquid form. Solvents can include water, alcohol and mixtures thereof.

If alcohols are used, they can be of the same carbon number or are the same alcohols from which the alkoxide bases themselves are derived. Thus, methanol would be a suitable solvent to use where the base is an alkali methoxide.

EXAMPLES

The preparation of acetyl p-toluenesulfonate. Acetyl p-toluenesulfonate was prepared according to published procedure by reaction of p-toluenesulfonic acid with acetyl chloride. The mixture of p-toluenesulfonic acid monohydrate (50 g, 0.26 mol) in toluene (100 mL) was refluxed in a Dean-Stark apparatus for 3 hours to effect dehydration and the toluene was then evaporated under vacuum. To the residue, acetyl chloride (80 mL, 1 mol) was added and the reaction mixture was refluxed for 5 hours. Then, the excess of acetyl chloride was removed under vacuum to give crude acetyl p-toluenesulfonate (56 g), which contained approximately 25% of p-toluenesulfonic anhydride (according to the NMR spectrum). The crude anhydride was used for further experiments.

The preparation of 2-[2-(p-toluenesulfonyloxy)ethoxy] ethyl acetate. This reaction was carried out under neat conditions, that is, no additional solvent was added, the dioxane functioning as both solvent and reactant. The mixture of acetyl p-toluenesulfonate (25 g; contain approximately 18.8 g, 0.088 mol of acetyl p-toluenesulfonate and 6.2 g of p-toluene sulfonic anhydride) in 1,4-dioxane (54 mL, 0.53 mol) was refluxed (101° C.) for 50 hours. The reaction progress was monitored by NMR. New sets of multiplets in the range 3.61-3.75 ppm and 4.13-4.18 ppm, which appeared in the $^1$H NMR spectrum, were assigned to the ethylene glycol fragments of 2-[2-(p-toluenesulfonyloxy)ethoxy]ethyl acetate. According to the NMR data, the approximate degree of conversion was 40-45% after 50 hours of reflux. After 90 hours of reflux the excess 1,4-dioxane was evaporated under vacuum to give 2-[2-(p-toluene-sulfonyloxy)ethoxy]ethyl acetate (21.3 g, 80% yield) of 90% purity, as an oil. $^1$H NMR δ 2.08 (s, 3H), 2.46 (s, 3H), 3.64 (t, J=4.8 Hz, 2H), 3.70 (t, J=4.8 Hz, 2H), 4.14-4.20 (m, 4H), 7.37 (d, J=8.2 Hz, 2H), 7.81 (d, J=8.2 Hz, 2H); $^{13}$C NMR δ 20.7, 21.5, 63.2, 68.5, 68.6, 69.1, 127.8, 129.7, 129.8, 144.8, 170.8.

The reported time in the literature as required for the preparation of 2-[2-(p-toluenesulfonyloxy)ethoxy]ethyl acetate in 87% yield, was 24 hours in acetonitrile solvent [68JACS3878, 71JOC532]. Therefore, an additional run was carried out in acetonitrile solution. The mixture of anhydride (7 g) and 1,4-dioxane (15 mL) in acetonitrile (30 mL) was refluxed (82° C.) for 24 hours. However, NMR analysis of the reaction mixture showed only 3-5% conversion.

Based on the above experimental data, higher temperature for the reaction mixture is required to promote the process of cleavage.

The preparation of 2-[2-(p-toluenesulfonyloxy)ethoxy] ethyl acetate at 134-137° C. in a sealed tube. The mixture of acetyl p-toluenesulfonate (1 g) in dioxane (2.2 g, 5.5 equivalents) was stirred in a sealed tube at 134-137° C. for 18 hours to complete conversion (the NMR analysis of the reaction mixture after 8 hours showed approximately 50-60% conversion). Water was then added and the product was extracted with diethyl ether. The extract was dried over magnesium sulfate and solvent was evaporated in vacuum to give 2-[2-(p-toluenesulfonyloxy)ethoxy]ethyl acetate (1 g, approximately 70%) of 90% purity.

The preparation of 2-(2-t-butylaminoethoxy)ethyl acetate. A mixture of 2-[2-(p-toluenesulfonyloxy)ethoxy]ethyl acetate (3.6 g, 0.012 mol) with t-butylamine (6.95 g, 0.095 mol) in toluene was refluxed for 12 hours. The reaction mixture was then cooled to 0° C. and kept for 1 hour at this temperature. The mixture was filtered to remove t-butylammonium p-toluenesulfonate and solvent was evaporated under vacuum to give 2-(2-t-butylaminoethoxy)ethyl acetate (2.4 g, 99%) as liquid. $^1$H NMR δ 1.14 (s, 9H), 2.08 (s, 3H), 2.79 (t, J=5.5 Hz, 2H), 3.61-3.68 (m, 4H), 4.22 (t, J=4.7 Hz, 2H); $^{13}$C NMR δ 20.8, 28.6, 41.8, 50.5, 63.4, 68.7, 70.8, 170.9.

Preparation of 2-(2-t-butylaminoethoxy)ethanol (EETB). 2-(2-t-Butylaminoethoxy)ethyl acetate (1.2 g, 5.9 mmol) was stirred for 7 hours with sodium methoxide (0.015 g, 0.28 mmol) in methanol (15 mL) at room temperature. The NMR analysis of the reaction mixture showed approximately 20% conversion. Additional sodium methoxide (0.015 g, 0.28 mmol) was added to the reaction mixture and it was stirred for an additional 3 hours. Solvent was evaporated and the liquid phase was separated from the solid by filtration. The solid was washed with diethyl ether. The combined filtrates were evaporated under reduced pressure to remove a solvent to give 2-(2-t-butylamino-ethoxy)ethanol (EETB) as yellowish liquid (0.65 g, 70%) $^1$H NMR δ 1.12 (s, 9H), 2.76 (t, J=5.1 Hz, 2H), 3.59-3.66 (m, 4H), 3.70-3.73 (m, 2H); $^{13}$C NMR δ 28.8, 42.2, 50.3, 61.8, 71.3, 72.6.

This reaction was repeated using 0.1 equivalent of sodium methoxide. The mixture of 2-(2-tert-butylaminoethoxy)ethyl acetate (1.0 g, 4.9 mmol) with sodium methoxide (0.03 g, 0.56 mmol) in methanol (15 mL) was stirred for 3 hours at room temperature. The NMR analysis of the reaction mixture showed no signals of 2-(2-t-butylaminoethoxy)ethyl acetate. Solvent was evaporated and the liquid phase was separated from the solid by filtration. The solid was washed with diethyl ether. The combined filtrates were evaporated under reduced pressure to remove a solvent to give EETB (0.55 g, 70%).

Hydrolysis of 2-(2-t-butylaminoethoxy)ethyl acetate with NaOH. A 2N solution of NaOH in methanol (3 mL, 6 mmol) was added to a solution of 2-(2-t-butylaminoethoxy)ethyl acetate (1 g, 5 mmol) in methanol (5 mL) and the reaction mixture was refluxed for 3 hours. The reaction mixture was evaporated and diethyl ether was added to the residue. The suspension that formed was filtered and the precipitate was washed with diethyl ether. The filtrate was evaporated under vacuum and diethyl ether was added to the residual oil to precipitate sodium salts. This solution was filtered and the solvent was removed under vacuum to give a yellowish oil (0.9 g). The NMR analysis of this oil showed the desired product, 2-(2-tert-butylamineethoxy)ethanol (EETB) in approximately 90% purity.

The preparation of acetyl p-toluenesulfonate from acetic anhydride. Acetyl p-toluenesulfonate was prepared according to published procedure by reaction of p-toluenesulfonic acid monohydrate (50 g, 0.26 mol) in toluene (100 mL). Toluene was refluxed in a Dean-Stark apparatus for 3 h to remove water and the toluene was then evaporated under vacuum. To the residue, acetic anhydride (47 mL, 51 g, 0.5 mol) was added and the reaction mixture was stirred at 130° C. for 1 h. Acetic acid and the excess of acetic anhydride were removed under vacuum (bath 50-60° C., 3 mm of Hg) to give crude acetyl p-toluenesulfonate (55 g, dark brown solid) of approximately 50% purity (according to NMR spectra), which contained unreacted p-toluenesulfonic acid and anhydride.

The one-step preparation of 2-[2-(p-toluenesulfonyloxy)ethoxy]ethyl acetate. The mixture of acetic anhydride (1.8 g, 1.7 mL, 0.018 mol) with anhydrous p-toluenesulfonic acid (2.7 g, 0.016 mol) in 1,4-dioxane (4 mL, 0.047 mol) was stirred in a sealed tube at 130-135° C. for 24 h (the time required for complete conversion of p-toluenesulfonic acid. The reaction was monitored by NMR. Water was added and product was extracted with diethyl ether. The solvent was evaporated in vacuum to give 2-[2-(p-toluenesulfonoxy)ethoxy]ethyl acetate (3.7 g, 78% yield) of 90-95% purity, as oil $^1$H NMR $\delta$2.08 (s, 3H0, 2.46 (s, 3H), 3.64 (t, J=4.8 Hz, 2H0, 4.14-4.20 (m, 4), 7.37 (d, J=8.2 Hz, 2H), 7.81 (d, –8.2 Hz, 2H); $^{13}$C NMR $\delta$ 20.7, 21.5, 63.2, 68.5, 68.6, 69.1, 127.8, 129.7, 129.8, 144.8, 170.8.

The one-vessel preparation of 2-(2-tert-butylaminoethoxy)ethyl acetate. The mixture of acetic anhydride (1.3 g, 1.2 mL, 12.7 mmol) with anhydrous p-toluenesulfonic acid (2.0 g, 11.6 mmol) in 1,4-dioxane (3 mL, 3.1 g, 35 mmol) was stirred in a sealed tube at 130-135° C. for 24 h. The reaction mixture was cooled to room temperature and tert-butylamine (6.8 g, 9.8 mL, 0.093 mol) was added followed by stirring of this mixture at 120-125° C. for 6 h. The reaction mixture was cooled to room temperature and water was added. The product was extracted with diethyl ether, the extract dried over magnesium sulfate and the solvent evaporated in a vacuum to give 2-(2-tert-butylaminoethoxy)ethyl acetate (1.4 g, 60%) as liquid. $^1$H NMR $\delta$ 1.14 (s, 9H0, 2.08 (s, 3H), 2.79 (t, J–5.5 Hz, 2H), 3.61-3.68 (m, 4H), 4.22 (t, J–4.7 Hz, 2H); $^{13}$C NMR $\delta$ 20.8, 28.6, 41.8, 50.5, 63.4, 68.7, 70.8. 170.9.

The preparation of 2-(2-tert-butylaminoethoxy)ethanol (EETB). The mixture of 2-(2-tert-butylaminoethoxy)ethyl acetate (1.8 g, 8.85 mmol) with sodium hydroxide (0.36 g, 9.0 mmol) in methanol (9 mL) was refluxed for 3 h. The mixture was cooled to room temperature and the solid was filtered (0.887 g, approx. 117%). The solid was washed with diethyl ether. The combined organic filtrates were concentrated in vacuum, the solid part was filtered off and washed with diethyl ether. The filtrate was concentrated in vacuum to give the EETB product (0.75 g, approx. 60% as oil. $^1$H NMR $\delta$ 1.12 (s, n9H), 2.76 (t, J–5.1 Hz, 2H), 3.59-3.66 (m, 4H), 3.70-3.73 (m, 2H)p $^{13}$C NMR $\delta$ 28.8, 42.2, 50.3, 61.8, 1.3, 72.67.

Preparation of 2-(2-tert-butylaminoethoxy)ethyl acetate. A 15 mL sealed tube was charged with a solution of 2-[2-(p-toluenesulfonyloxy)ethoxy]ethyl acetate (2 g, 6.6 mmol, 1 eq) and tert-butyl amine (3.87 g, 52.92 mmol, 5.6 mL, 8 eq.) in dry toluene (6 mL). The mixture was stirred at 120° C. for 3 h. Reaction progress was monitored by TLC and NMR each one hour. The reaction mixture was cooled room temperature and filtered; the precipitate was washed with toluene. The filtrate was partially evaporated under vacuum to remove tert-butylamine. The residue was filtered and the precipitate was washed with toluene. The filtrate was evaporated in vacuum to give yellow residual oil (1.18 g, 88% yield). The NMR spectrum showed 2-(2-tert-butylaminoethoxy)ethyl acetate of 95-97% purity.

Preparation of 2-(2-tert-butylaminoethoxy)ethanol. The crude 2-(2-tert-butylaminoethoxy)ethyl acetate product (0.5 g, 2.47 mmol) was refluxed with 3.7 mmol of NaOH in methanol (10 mL) for 1 h followed by evaporation under vacuum, extraction with diethyl ether and removal of solvent under vacuum to give a yellow oil (0.3 g, 77% yield), confirmed by NMR to be 2-(2-tert-butylaminoethoxy)ethanol of 95-97% purity.

The preparation of diphenylketene. The preparation of diphenylketene was carried out according to the published procedure starting from diphenylacetic acid. [Taylor, E. C., et al., Org Synth CV 6, 549.]

A. Diphenylacetyl chloride. A 500 mL, three-necked flask equipped with a dropping funnel and a reflux condenser carrying a calcium chloride drying tube was charged with diphenylacetic acid (50.0 g, 0.236 mol) and anhydrous toluene (150 mL). The mixture was heated under reflux, and thionyl chloride (132 g, 80.1 mL, 1.11 mol) was added dropwise over 30 minutes. Refluxing was continued for 7 additional hours and then the toluene and excess thionyl chloride were removed by distillation under reduced pressure. The residue was dissolved in 150 mL of refluxing, anhydrous hexane. The hot solution was treated with charcoal and filtered, and the filtrate was cooled to 0° C. in a sealed flask. The product, which crystallizes as colorless plates was filtered, washed with a little cold hexane, dried at 25° C. under vacuum giving diphenylacetyl chloride (46 g, 85%), m.p. 51-52° C.

B. Diphenylketene. A 500 mL, three-necked flask equipped with a magnetic stirring bar and a dropping funnel was charged with a solution of diphenylacetyl chloride (46.0 g, 0.2 mol) in anhydrous diethyl ether (300 mL) under a nitrogen atmosphere. The flask was cooled in an ice bath and triethylamine (21.25 g, 0.21 mol) was added dropwise over 30 minutes to the stirred solution; triethylamine hydrochloride precipitates as a colorless solid, and the ether becomes bright yellow in color. When addition of the triethylamine was complete, the flask was tightly stoppered and stored overnight at 0° C. The triethylamine hydrochloride was separated by filtration (under a nitrogen atmosphere) and washed with anhydrous ether (approx. 80-100 mL) until the washings were colorless. The ether was removed under reduced pressure and the residual red oil was transferred to a distilling apparatus fitted with a short Vigreux column and distilled (rapidly) giving diphenylketene (23.5 g, 61%), as an orange oil, b.p. 116-121°/1 mm of Hg (Lit. b.p. 118-120/1 mm of Hg.

The preparation of diphenylacetyl p-toluenesulfonate. A 100-mL, flask equipped with a magnetic stirring bar and Dean-Stark apparatus was charged with p-toluenesulfonic acid monohydrate (9.51 g, 0.05 mol) and toluene (60 mL). The mixture was refluxed for 2 h to remove water and toluene was distilled off to 10 mL volume at normal pressure. This residue was cooled to 20-25° C. and added dropwise to a stirred solution of diphenylketene (9.7 g, 0.05 mol) in anhydrous diethylether (20 mL) at 0-5° C. over 3-5 min. The orange solution of diphenylketene became slightly yellow; the reaction mixture was stirred for 6 h at 0-5° C. The formed precipitate was filtered under a nitrogen atmosphere, washed with anhydrous diethyl ether (15 mL) and dried in a nitrogen flow giving diphenylacetyl toluenesulphonate (12.3 g, 67%), as off white prisms, m.p. 84-87° C. (decomposition). $^1$H NMR (CDCl$_3$) $\delta$ 2.43 (s, 3H), 5.01 (s, 1H), 7.10-7.16 (m, 4H), 7.24-7.32 (m, 8H), 7.82 (d, J=7.9 Hz, 2H); $^{13}$C NMR (CDCl$_3$) δ 21.7, 57.0, 127.8, 128.4, 128.8, 129.0, 129.6, 132.6, 136.2, 146.0, 165.5. Anal. Calcd. for C$_{21}$H$_{18}$O$_4$S (366.44): C, 68.83; H, 4.95. Found: C, 68.61; H, 4.89.

Cleavage of 1,4-dioxane with diphenylacetyl p-toluenesulfonate: the preparation of 2-[2-(p-toluenesulfonyloxy)ethoxy]ethyl diphenylacetate. A 20 mL sealed tube was charged with diphenylacetyl toluenesulphonate (2.0 g, 5.5 mmol) and 1,4-dioxane (2.4 g, 27.5 mmol) under a nitrogen atmosphere. The mixture was stirred at 130-135° C. for 18 h. The $^1$H NMR spectrum of the sample showed two triplets at 4.08 ppm and 4.23 ppm, and a multiplet at 3.50-3.62 ppm, which were assigned to 2-[2-(p-toluenesulfonyloxy)ethoxy]ethyl diphenylacetate. Approximate degree of conversion of diphenylacetyl toluene-sulphonate was 25-30% according to NMR. The reaction mixture was stirred at 145-150° C. for an additional 15 h. The $^1$H NMR spectrum of the sample showed approximately 75-80% conversion. The solvent was evaporated under reduced pressure and the residue was purified by column chromatography on silica gel using a mixture of ethyl acetate/hexanes 1/3 as an eluent to give 2-[2-(p-toluenesulfonyloxy)ethoxy]ethyl diphenylacetate (1.35 g, 56%), as a yellow oil. $^1$H NMR δ 2.42 (s, 3H), 3.53-3.61 (m, 4H), 4.08 (t, J=4.7 Hz, 2H), 4.23 (t, J=4.7 Hz, 2H), 5.05 (s, 1H), 7.25-7.33 (m, 12H), 7.77 (d, J=8.2 Hz, 2H); $^{13}$C NMR δ 21.6, 56.9, 64.0, 68.5, 69.0, 69.0, 127.3, 127.9, 128.5, 128.6, 129.8, 138.5, 144.8, 172.3. Anal. Calcd. for C$_{25}$H$_{26}$O$_6$S (454.55): C, 66.06; H, 5.77. Found: C, 66.18; H, 5.85.

The preparation of 2-(2-tert-butylaminoethoxy)ethyl diphenylacetate. The mixture of 2-[2-(p-toluenesulfonyloxy)ethoxy]ethyl diphenylacetate (0.9 g, 2 mmol) with tert-butylamine (1.7 mL, 1.2 g, 16 mmol) in toluene (20 mL) was gently refluxed for 24 h. The reaction mixture was then cooled to room temperature. The precipitate formed was filtered and washed with toluene. The filtrate was partially concentrated to remove excess tert-butylamine, and filtered again. The solvent was evaporated in a vacuum to give 2-(2-tert-butylaminoethoxy)ethyl diphenylacetate (0.67 g, 95%) as a yellow liquid. $^1$H NMR δ 1.09 (s, 9H), 2.08 (s, 3H), 2.69 (t, J=5.4 Hz, 2H), 3.52 (t, J=5.4 Hz, 2H), 3.64 (t, J=4.8 Hz, 2H), 4.30 (t, J=4.8 Hz, 2H), 5.06 (s, 1H), 7.24-7.32 (m, 10H); $^{13}$C NMR δ 28.9, 42.0, 50.1, 57.0, 64.2, 68.7, 71.3, 127.2, 128.6, 128.6, 138.6, 172.4.

The preparation of 2-(2-tert-butylaminoethoxy)ethanol (EETB). A 2N solution of sodium hydroxide in methanol (0.8 mL, 1.6 mmol) was added to a solution of 2-(2-tert-butylaminoethoxy)ethyl diphenylacetate (0.5 g, 1.41 mmol) in methanol (5 mL). The reaction mixture was refluxed for 5 h. The mixture was cooled to room temperature and the precipitate was filtered. The precipitate was washed with diethyl ether. The filtrate was concentrated under vacuum, diethyl ether was added to the residue and the suspension was filtered (precipitate was washed with diethyl ether). The filtrate was evaporated under vacuum to give the product EETB (0.22 g, approx. 97%) as a colorless oil.

The invention claimed is:

1. A method for the synthesis of severely sterically hindered secondary aminoether alcohols of the formula

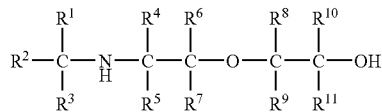

wherein R$^1$ and R$^2$ are each selected from the group consisting of alkyl, hydroxylalkyl radicals having 1 to 4 carbon atoms or in combination with the carbon atom to which they are attached they form a cycloalkyl group having 3 to 8 carbon atoms, and R$^3$ is selected from the group consisting of hydrogen, alkyl or hydroxyalkyl radicals having 1 to 4 carbon atoms, and R$^4$, R$^5$, R$^6$, R$^7$, R$^8$, R$^9$, R$^{10}$ and R$^{11}$ are the same or different and are selected from the group consisting of hydrogen, alkyl and hydroxyalkyl radicals having 1 to 4 carbons provided that at least one of R$^4$ or R$^5$ bonded to the carbon atom directly bonded to the nitrogen atom is an alkyl or hydroxyalkyl radical when R$^3$ is hydrogen, the process involving reacting an acid halide or organic carboxylic acid anhydride, a ketene, or mixture of any two or of all three thereof, of the formula

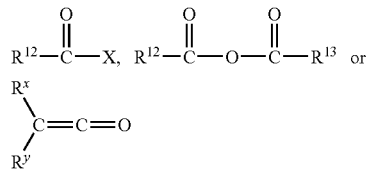

wherein R$^{12}$ and R$^{13}$ are the same or different and each is selected from the group consisting of alkyl radicals having 1 to 4 carbon atoms, aryl radicals bearing hydrogen or C$_1$-C$_{10}$ alkyl groups substituted thereon, and mixtures thereof, X is halogen selected from the group consisting of F, Cl, Br, I, and mixtures thereof, and R$^x$ and R$^y$ are the same or different and are selected from the group consisting of hydrogen, alkyl radicals having 1 to 4 carbon, aryl radicals bearing substituents selected from the group consisting of hydrogen and one or more alkyl radicals, and mixtures thereof, or R$^x$ and R$^y$ in combination with the carbon to which they are attached form a cycloalkyl radical having 3 to 8 carbons, with an organic sulfonic acid of the formula

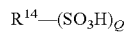

wherein Q is an integer selected from 1 to 4, R$^{14}$ is selected from the group consisting of alkyl radicals having 1 to 4 carbon atoms, haloalkyl radicals of the formula C$_n$H$_{(2n+1)-z}$X$_z$ wherein n is 1 to 4, X is selected from the group consisting of F, Cl, Br, I, and mixtures thereof, and z ranges from 1 to 5, aryl radicals of the formula

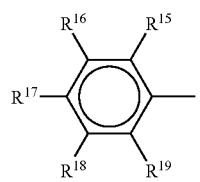

wherein R$^{15}$, R$^{16}$, R$^{17}$, R$^{18}$, and R$^{19}$ are the same or different and are selected from hydrogen and alkyl radicals having 1 to 20 carbon atoms, and mixtures thereof, to yield an acyl sulfonate of the formula

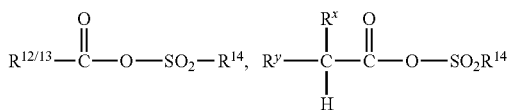

or mixtures thereof, which is then reacted with a dioxane of the formula

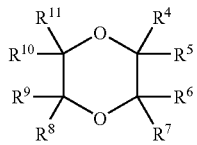

wherein $R^4$, $R^5$, $R^6$, $R^7$, $R^8$, $R^9$, $R^{10}$, and $R^{11}$ are the same or different and are selected from hydrogen, alkyl and hydroxyalkyl radicals having 1 to 4 carbons to yield

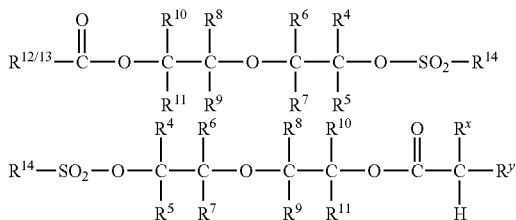

or mixtures thereof, which is then aminated with an alkylamine of the formula

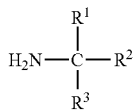

wherein $R^1$, $R^2$, and $R^3$ are as previously defined to yield

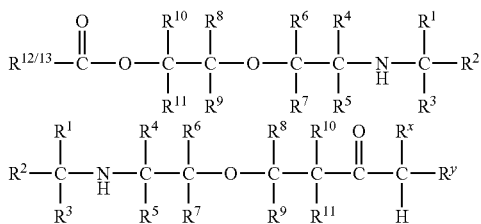

or mixtures thereof, which is then hydrolyzed with base to yield

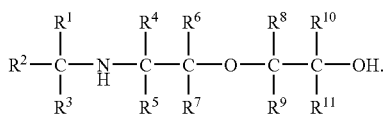

2. The method of claim 1 for the synthesis of severely sterically hindered secondary aminoether alcohols using the acid halide of the formula

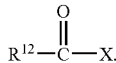

3. The method of claim 1 for the synthesis of severely sterically hindered secondary aminoether alcohols using the organic carboxylic acid anhydride of the formula

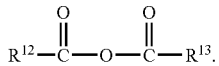

4. The method of claim 1 for the synthesis of severely sterically hindered secondary aminoether alcohols using ketene, of the formula

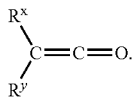

5. The method according to claim 1, 2, 3 or 4 wherein $R^1$, $R^2$ and $R^3$ are methyl radicals.

6. The method according to claim 1, 2, 3 or 4 wherein $R^4$, $R^5$, $R^6$, $R^7$, $R^8$, $R^9$, $R^{10}$, $R^{11}$, are hydrogen and $R^x$ and $R^y$ are hydrogen or phenyl.

7. The method according to claim 1, 2, 3 or 4 wherein $R^{15}$, $R^{16}$, $R^{18}$, and $R^{19}$ are hydrogen and $R^{17}$ is hydrogen or methyl.

8. The method according to claim 1, 2, 3 or 4 wherein the base is selected from alkali metal hydroxide alkali metal alkoxide, alkali metal carbonate.

9. The method according to claim 1, 2, 3 or 4 wherein $R^1$, $R^2$ and $R^3$ are methyl, $R^4$, $R^5$, $R^6$, $R^7$, $R^8$, $R^9$, $R^{10}$, and $R^{11}$ are hydrogen, $R^{15}$, $R^{16}$, $R^{18}$, and $R^{19}$ are hydrogen, $R^{17}$ is hydrogen or methyl and $R^x$ and $R^y$ are hydrogen or phenyl.

10. The method of claim 1, 2, 3 or 4 wherein the acyl sulfonate is made by reacting organic carboxylic acid halide, organic carboxylic acid anhydride, ketene, mixtures of any two or of all three thereof with the organic sulfonic acid at a temperature in the range of about −20 to 150° C. at a pressure between about 1 bar to 100 bars, the acyl sulfonate is reacted with dioxane at a dioxane to acyl sulfonate ratio of about 1:1 to about 10:1 at a temperature between about 50° C. to about 200° C., the resulting cleavage product is reacted with alkyl amine in an amine to cleavage product sulfonate group ratio in the range of about stoichiometric to about 10:1 at a pressure of about atmospheric (1 bar) to about 100 bars, at a temperature of about 40° to about 200° C., and wherein the aminated product is hydrolyzed with base at between about 20° C. to about 110° C.

11. The method of claim 1, 2, 3 or 4 wherein the mixing of the anhydride, acid halide, ketene or mixture of any two or of all three thereof, the organic sulfonic acid and the dioxane is combined in a single step, the reaction mixture being heated at a temperature between about 50° C. to about 200° C. to produce a cleavage product, the cleavage product and the alkylamine being reacted at an amine to cleavage product ratio ranging from about stoichiometric to about 10:1 at a pressure of about atmospheric (1 bar) to about 100 bars, at a temperature of about 40° C. to about 200° C., and wherein the aminated product is hydrolyzed with base at between about 20° C. to about 110° C.

12. The method of claim 1, 2, 3 or 4 wherein Q is 1.

\* \* \* \* \*